United States Patent
Aharonov et al.

(10) Patent No.: US 10,010,082 B2
(45) Date of Patent: Jul. 3, 2018

(54) **PESTICIDE FOR THE EXTERMINATION OF *BLATTELLA GERMANICA* AND A METHOD FOR PRODUCING THEREOF**

(71) Applicants: Igor Aharonov, Ashdod (IL); Roman Kabilov, Ashdod (IL); Daniel Daniel, Ashdod (IL)

(72) Inventors: Igor Aharonov, Ashdod (IL); Roman Kabilov, Ashdod (IL); Daniel Daniel, Ashdod (IL)

( * ) Notice: Subject to any disclaimer, the term of this patent is extended or adjusted under 35 U.S.C. 154(b) by 0 days.

(21) Appl. No.: 15/157,415

(22) Filed: May 18, 2016

(65) Prior Publication Data

US 2016/0338357 A1     Nov. 24, 2016

(30) Foreign Application Priority Data

May 19, 2015 (IL) .......................................... 238908

(51) Int. Cl.
*A01N 59/14* (2006.01)
*A01N 25/00* (2006.01)

(52) U.S. Cl.
CPC .................... *A01N 59/14* (2013.01)

(58) Field of Classification Search
CPC .............................. A01N 59/14; A01N 25/006
See application file for complete search history.

(56) References Cited

U.S. PATENT DOCUMENTS

| | | | | |
|---|---|---|---|---|
| 4,299,258 A * | 11/1981 | Brite | ...................... | A01N 25/00 141/1 |
| 4,438,090 A * | 3/1984 | Brite | ...................... | A01N 25/00 424/10.31 |
| 4,461,758 A * | 7/1984 | Brite | ...................... | A01N 25/00 424/10.31 |
| 5,346,700 A * | 9/1994 | Stapleton | ............. | A01N 25/006 424/409 |
| 5,484,588 A * | 1/1996 | Ogino | .................. | A01N 25/006 424/84 |
| 5,705,176 A * | 1/1998 | Stapleton | ............. | A01N 25/006 424/409 |
| 6,007,832 A * | 12/1999 | Stapleton | ............. | A01N 25/006 424/409 |

FOREIGN PATENT DOCUMENTS

| | | | | |
|---|---|---|---|---|
| GB | 2302506 | 1/1997 | | |
| KR | 20130143467 | 12/2013 | | |
| WO | WO 2012107266 A1 * | 8/2012 | ........... | A01N 25/006 |

* cited by examiner

*Primary Examiner* — Robert A Wax
*Assistant Examiner* — Olga V Tcherkasskaya
(74) *Attorney, Agent, or Firm* — Edward Langer, ADV & Patent Attorney

(57) ABSTRACT

A pesticide for the extermination of an insect of the order Blattodea, and particularly of *Blattella germanica*, the pesticide comprising a uniform mixture of: a *Blattella germanica* attractant comprising about 75% cooked mashed potatoes and about 14% cooked eggs yolk; and an active ingredient comprising boric acid in a concentration of about 10%, thereby providing a non-toxic to humans or pets pesticide which attracts the insect, and upon consuming it by the insect, the active ingredient exterminates the insect.

11 Claims, No Drawings

PESTICIDE FOR THE EXTERMINATION OF *BLATTELLA GERMANICA* AND A METHOD FOR PRODUCING THEREOF

TECHNICAL FIELD

The present invention relates to the field of pesticides. More particularly, the invention relates to a method and substance for exterminating Blattodea, and particularly *Blattella germanica*.

BACKGROUND OF THE INVENTION

Insect infestation is a nuisance to all households and businesses around the world. There are many different types of exterminating methods and substances that are used for different types of insects, such as ants, cockroaches, flies, etc.

The German cockroach, a.k.a *Blattella germanica*, is particularly associated with restaurants, food processing facilities, hotels, and institutional establishments such as nursing homes. It is very small, and therefore can hide in extremely small spaces and even in cracks. It reproduces faster than any other residential cockroach, and produces dozens of nymphs from each egg. The German cockroach is resilient in the face of many pest control measures. When pesticides are used against it, the vicinity must be evacuated from living creatures, which leads to loss of working days and therefore, loss of income. Even if the vicinity has been successfully cleaned out of cockroaches, it won't be long until they return within a carton of food supplies from outside the institution.

All of the above deem the German cockroach a major problem to institutions. There is a need for a solution to the constant infestation of the German cockroach.

It is an object of the present invention to provide a solution to the above-mentioned and other problems of the known substances for exterminating cockroaches.

Particularly, it is an object of the present invention to provide a pesticide which exterminates Blattodea, and particularly the *Blattella germanica*.

Other objects and advantages of the invention will become apparent as the description proceeds.

SUMMARY OF THE INVENTION

The term "active ingredient" refers herein as to an ingredient that exterminates an object thereof, and in this case exterminates Blattodea, and particularly of *Blattella germanica*.

In one aspect, the present invention is directed to a pesticide for the extermination of an insect of the order Blattodea, and particularly of *Blattella germanica*, the pesticide comprising a uniform mixture of;
 a *Blattella germanica* attractant comprising cooked mashed potatoes and cooked eggs yolk; and
 an active ingredient comprising boric acid in a concentration of between 9 and 11 percents by weight, thereby providing a non-toxic to humans or pets pesticide;
 thereby the pesticide attracts the insect, and upon consuming it by the insect, the active ingredient exterminates the insect.

Preferably, the mixture comprises about 5 parts by weight of mashed potatoes for 1 part by weight of eggs yolk.

The mixture may further comprise about 1% of preservatives such as of sodium benzoate, for prolonging a shelf life of the pesticide, and less than 0.008% by weight of ingestion repellent, such as Denatonium benzoate.

Preferably, the potatoes are of red potato species.

The pesticide may be in a paste like texture. However, preferably the pesticide is in a form of lumps form of dimensions between 1 and 3 cm, such as balls of a diameter of 2 cm, cylinders of a diameter of 1 cm a length of 3 cm, and so on.

The pesticide may be distributed as units packed into a sealed package, for preserving freshness and shelf life thereof.

The pesticide may be used occasionally on an infected area, and also permanently within an area for the purpose of preventing a recurrence of infestation of the *Blattella germanica*.

In experiments made by the Applicant the following portions have been found as most effective:
 a uniform mixture of:
 about 75% by weight of cooked mashed potatoes;
 about 14% by weight of cooked eggs yolk;
 about 10% by weight of boric acid; and
 about 1% by weight of preservatives; and
 less than 0.008% by weight of ingestion repellent, such as Denatonium benzoate;
thereby providing a non-toxic to humans or pets pesticide, which has a "long" shelf life.

It should be noted that the active ingredient is a boric acid in a concentration of about 10%. A higher concentration may cause some of the cockroaches to be repulsed by the pesticide rather than being attracted to it, while a lower concentration may be less effective.

The pesticide of the present invention may further comprise less than 0.008% of ingestion repellent such as Denatonium benzoate, in order to be rejected from swallowing by human beings and pets.

The pesticide may be distributed also in a form of liquid and gel, in a box of in a sealed syringe, made for example of plastic.

In another aspect, the present invention is directed to a method for producing a pesticide for extermination of insects of the order Blattodea, and particularly of *Blattella germanica*, the method comprising the steps of:
 cooking potatoes until shells thereof can be peeled;
 cooking eggs yolk until getting harden;
 mixing the cooked potatoes, the cooked eggs yolk, between 9 and 11% of boric acid and optionally 0.5 to 2% of preservatives, until a uniform mixture is obtained;
 drying the mixture; and
 dispensing lumps of about dimensions between 1 to 3 cm each.

DETAILED DESCRIPTION OF THE INVENTION

The present invention will be understood from the following detailed description of preferred embodiments ("best mode"), which are meant to be descriptive and not limiting. For the sake of brevity, some well-known features, methods, systems, procedures, components, and so on, are not described in detail.

The food that was found to attract and kill the insects of the order Blattodea (cockroaches), and particularly *Blattella germanica*, is a mixture of cooked red potato and an egg yolk, particularly in a concentration of approximately 5 parts of mashed potatoes and 1 part of eggs yolk.

A mixture that was found mostly effective for *Blattella germanica* comprises the following ingredients: 75% cooked mashed potatoes, 14% eggs yolk, 10% boric acid, and 1% preservatives. Of course these concentrations may differ when it comes to a different Blattodea. Preferably, the mashed potatoes are peeled.

In a production process all the ingredients are mixed together until uniform dough is generated.

The potatoes are cooked until their peeling their shells is possible. Preferably the shells are removed. The eggs yolk is cooked until becoming hardened. In this state of aggregation, the mashed potatoes and their liquids, cooked eggs yolk, boric acid and the preservatives is mixed until obtaining a uniform mixture.

The mixture can be dried, e.g., by heating thereof, evaporation, and so on.

It should be noted that the active ingredient is a boric acid in a concentration of about 10%. A higher concentration may cause some of the cockroaches to be repulsed by the pesticide rather than being attracted to it, while a lower concentration may be less effective.

The mixture is obtained in a paste-like texture, and can be divided into several lumps, such as in ball shapes, in a diameter of approximately 1-3 cm each. The lumps can then be distributed all around the contaminated area. The lumps can also be safely distributed in a non-contaminated area as a means for preventing cockroach contamination. The lumps are merely an example, and other 3D forms can be used, such as cube, oval, and so on. Each dimension (length, width, height, and so on) of such an item is approximately 1-3 cm.

The pesticide lumps are stored in a sealed freshness preserving packaging. The packaging and the added preservative enhances the shelf life of the lumps, to up to two years. The packaging may be in a form of vacuum forming, but not only.

Since the pesticide is only toxic by consumption, and not by aspiration, it is therefore environmentally friendly. Lab testing's have proven that even consumption of the lumps by pets, is not toxic.

There is no need to vacate the contaminated area from people or pets, as is the case for most exterminating methods. The lumps are distributed in cabinets, drawers, corners, or any other place that may be inhabited by the cockroaches, and they may remain there as long as their expiry date allows them to be, while maintaining a regular routine in the contaminated area. Once the lumps expire (shrink due to dehydration), they may be replaced with fresh ones, and so, pesticide lumps may permanently be present so as to prevent any recurrence of the contamination by cockroaches.

The lumps may be distributed within the area by any person, so that there is no need for a certified exterminator, a fact which makes the use of these lumps cost effective.

EXAMPLES

A study has been conducted to determine boric acid ($H_3BO_3$) content in three batches of the pesticide formulation of the invention. The study has been conducted in compliance with Good Laboratory Practice (GLP) guidelines of the OECD.

Principle of the Method:

The study was done using a procedure using a colorimetric method based on the reaction of boron which is in the sample, with carmine acid in concentrated sulfuric acid to form a bluish red or blue compound, depending on the boron concentration. The color intensity is then measured spectrophotometrically at 585 nm in 1 cm cells. Boric acid standard was used for calibration and verification.

Sample Preparation:

The samples were weighed and subjected to extraction assisted by ultrasonification. After extraction and filtration the aliquot of the obtained was dissolved in a specified volume of water.

Method Verification:

The method verification was performed by determination of the following parameters:

1. Linearity—was demonstrated by preparation of boric acid solutions in the concentration range of 2.5-10 ppm of boron, addition of reagents, measurement of color intensity according to the test procedure and finally, linear regression construction.

The acceptance criterion was Linear regression coefficient $-R^2 \geq 0.995$.

2. Accuracy as deviation of linearity—After construction of the linear regression curve, the concentrations of all solutions will be recalculated according to the linear regression equation.

The acceptance criterion was accuracy within 90-110%.

3. System precision—Some standards were prepared and measured in triplicates. The system precision was calculated as RSD between replicates.

The acceptance criterion was RSD≤2%.

4. Method precision—one sample of the pesticide was chosen at random and the sample preparation and the boron determination was repeated six times. The method precision was calculated as the RSD between replicates.

The acceptance criterion was RSD≤5%.

5. Method recovery—One randomly chosen sample was prepared twice, and a known quantity of standard boric acid was added to the obtained solution. These spiked solutions were analyzed and the quantity of added standard was determined. The method recovery was calculated as the ratio of the found boron concentration to its nominal concentration, expressed as percent.

The acceptance criterion of the recovery falls between 90 and 110%.

Results:

The results are in Table I below, showing the concentration of boric acid found in each of the three analyzed batches of the present inventions pesticide.

TABLE I

| Batch | Ingredient | Specification Requirement | Result |
| --- | --- | --- | --- |
| 1 | Boric acid | 8.5-11.5% | 9.54% |
| 2 | Boric acid | 8.5-11.5% | 9.85% |
| 3 | Boric acid | 8.5-11.5% | 10.1% |

The results show that the concentration of boric acid in efficient compositions according to the invention, the active ingredient which terminates the *Blattella germanica* upon its consumption, was between 9.54% and 10.1%. These are considered low concentrations and are not toxic to humans or animals.

The efficiency of the present inventions pesticide has been tested and proved, as described herein below.

Efficiency Test of the Pesticide Against *Blattella germanica*:

All the testing's have been done on the *Blattella germanica*, a laboratory grown population mixed with a wild type population, in a controlled room, 12 hours of light per day, in a constant temperature of 28° C. (±2) and in 60-70% humidity.

Preliminary Testing:

Phase A: test with a number of samples without the active ingredient, for determining the preferred composition of ingredients of the attractants.

Phase B: testing of four samples with 5%, 10%, 20% and 30% of the active ingredient.

This preliminary testing was done in order to verify the non-toxicity of the attractants without the active ingredient.

Main Testing—determining the attracting efficiency of the pesticide with 10% active ingredient:

The tests were done in four open plastic crates, 65×40 cm, height 35 cm. The side walls were smeared with Teflon to avoid the exiting of the cockroaches from the crates.

Testing Steps:

Acclimation

On one side of each crate a piece of an egg carton was placed, which was used as a hiding place for the cockroaches.

On the other side a plate with alternative food (dog food) was placed on one corner.

On the second corner a plate with cotton and water was placed.

25 cockroaches were transferred into each crate; 5 females with an ootheca, 5 females without an ootheca, 10 mature young males three weeks post slough and 5 nymphes pre-maturation.

Bait Distribution

This step was carried out 48 hours post transfer of cockroaches into the crates, and after seeing that no harm was done to them.

24 hours pre-distribution, the bait was weighed in the amount of 1 g per plate—a large quantity in order to assure its presence throughout the entire testing.

Until distribution, the plates were kept exposed to air in the controlled room.

Bait distribution into the crates was executed in the evening, with weak and indirect lighting.

1. The plate with the dog food was replaced with a fresh batch.
2. The plate with the bait was placed in the second corner after being weighed once more.

For control purposes, in every crate a plate with bait was placed, which was protected from the cockroaches, in order to determine weight changes that might occur due to dehydration/humidity absorption.

In the morning, 12 hours post-bait distribution, the baits (both protected and exposed) were weighed for determining:

1. Weight change due to humidity/dehydration.
2. The amount that was consumed during the night The weighing as described above was performed also before and after the second night.

Once a day the dead cockroaches were counted and taken out of the crates

There was no need to add bait to the crates during the testing, since the eating was reduced. In the control crates however, food and bait was added since the eating was continued and becoming stronger.

Results:

1. Weight Changes

Table II—Percentage of weight change of the bait after application—as a result of dehydration/humidity absorption.

The results are an average of 4 repeats, with a deviation of ±10%

TABLE II

| During first 24 h (exposure to air) | During 24 h after entrance to the crate | During 20 additional days to air exposure |
| --- | --- | --- |
| 30% | 3% | 3% |

2. Eating

Table III—An average weight eaten by a cockroach during 12 hours at night.

The results are an average of 4 repeats, with a deviation of ±15%

TABLE III

|  | Bait | Dog food |
| --- | --- | --- |
| During $1^{st}$ night | 1.5 mg | 0.5 mg |
| During $2^{nd}$ night | 0.3 mg | 0.1 mg |

3. Death Rate

Table IV—The time in days required for death.

The results are from 4 repeats.

TABLE IV

| Start of Death | 25% Death | 50% Death | 75% Death | 90% Death | 100% Death |
| --- | --- | --- | --- | --- | --- |
| 1.5 | 2-3-4 | 4-5-6 | 9-11-13 | 15-22-35 | 18-29-47 |

Table V—Changes in cockroach population 47 days from beginning of experiment.

TABLE V

|  | Four Experimental Crates | Control 1 | Control 2 | Control Average |
| --- | --- | --- | --- | --- |
| No. of dead cockroaches taken out during the Experiment* | 25 from each crate | 12** | 7** |  |
| No. of Live Cockroaches*** | 0 | 245 | 280 | 263 |
| Size of population compared to beginning of Experiment | 0 | 980% | 1120% | 1090% |

*Not including young cockroaches that hatched in the experimental crates and died within a few days
**Mature cockroaches, old
***Cockroaches of different sizes, a few days old larva-mature

SUMMARY

1. Weight Change of the Bait:
    The fresh bait loses 30% of its initial weight, within the first day, due to air exposure. After that stage, the texture of the bait remains the same during the next 60 days.
2. Eating:
    The bait tested, without the active ingredient, was found to be suitable for use for the cockroaches. The addition of 10% of the active ingredient did not cause repulsion from the bait or decrease the eating amount. The toxic bait was eaten approximately 3 times more than the alternative food (dog food). The main eating was done on the first night. After the first night, the eating was reduced significantly, which is evidence to the harm that was done to the population.

3. Extermination:

The death of the cockroaches begun 36 hours after the distribution of the bait with the active ingredient.

50% extermination was achieved approximately 5 days from day 1. 90% extermination was achieved 15-35 days from day 1. 100% extermination was achieved within 18-47 days.

Additionally, young cockroaches that hatched from the ootheca in the crate at the time of the experiment, were exterminated within 7 days.

In the control crates—within 47 days of the experiment, a death rate of 35% of the cockroaches that were put into the crate (only old individuals) was achieved. However, reproduction in the crate brought the population to grow 10 times more. It should be noted that all the experiments were done along with preservative material, such as sodium benzoate.

CONCLUSIONS

Even though its activity is not rapid, the tested bait having 10% boric acid, is effective and is suitable for extermination of cockroaches in buildings.

Distribution of the bait in places that are protected from water, will bring to complete extermination of the cockroaches within a few weeks and will prevent the recurrence of the nuisance for a few months at least.

In order to achieve optimal results, the bait should be distributed in multiple places, in order to increase the chance of the cockroach finding the bait.

The foregoing description of the embodiments of the invention has been presented for the purposes of illustration. It is not intended to be exhaustive or to limit the invention to the above description in any form.

Any term that has been defined above and used in the claims, should be interpreted according to this definition.

The invention claimed is:

1. A pesticide for the extermination of an insect of *Blattella germanica*, said pesticide consisting of a uniform mixture of:
   a *Blattella germanica* attractant comprising 4 to 7 parts by weight of cooked mashed potatoes and 1 part by weight of cooked eggs yolk;
   an active ingredient comprising boric acid in a concentration of between 5 to 11 by weight percents, thereby providing a non-toxic to humans or pets pesticide; and
   0.5% to 1.5% by weight of preservatives;
   up to 0.008% by weight of ingestion repellent;
thereby said pesticide attracts said insect, and upon being consumed by said insect, said active ingredient exterminates said insect.

2. The pesticide of claim 1, wherein said ingestion repellent is denatonium benzoate.

3. The pesticide of claim 1, wherein said preservatives are of sodium benzoate, thereby prolonging a shelf life of said pesticide.

4. The pesticide of claim 1, wherein said potatoes are of a red potato species.

5. The pesticide of claim 1, wherein said pesticide is in a paste like texture.

6. The pesticide of claim 1, wherein said pesticide is in a form of lumps having dimensions between 1 cm and 3 cm.

7. The pesticide of claim 1, wherein said pesticide is divided into units packed into a sealed package, for preserving freshness and shelf life thereof.

8. A method for producing a pesticide for extermination of insects of *Blattella germanica*, the method comprising the steps of:
   cooking potatoes until shells thereof can be peeled;
   cooking egg yolks until getting hardened;
   mixing 4 parts to 7 parts by weight of said cooked potatoes, with 1 part by weight of said cooked egg yolks, between 9% to 11% by weight of boric acid and 0.5% to 2% by weight of preservatives, and 0.008% by weight of ingestion repellent until a uniform mixture is obtained;
   drying said mixture; and
   dispensing lumps of about dimensions between 1 cm to 3 cm each.

9. The method of claim 8, further comprising the step of using said pesticide within an area for the purpose of preventing an infestation or a recurrence thereof of the *Blattella germanica*.

10. A pesticide for the extermination of an insect of *Blattella germanica*, said pesticide consisting of a uniform mixture of:
    between 72 to 77% by weight of cooked mashed potatoes;
    between 13 to 15% by weight of cooked egg yolks;
    between 9.5% to 10.5% by weight of boric acid;
    between 0.5 to 1.5% by weight of preservatives; and
    up to 0.008% by weight of denatonium benzoate ingestion repellent, wherein said pesticide is in a form of liquid or gel, packed in a sealed syringe for preserving freshness and easy distribution of said pesticide;
thereby providing an efficient pesticide which is non-toxic to humans or pets.

11. The method of claim 8, further comprising the step of using said pesticide within a *Blattella germanica* infected area, for the purpose of exterminating *Blattella germanica* in said area.

* * * * *